United States Patent
Fisher et al.

(10) Patent No.: US 9,468,768 B2
(45) Date of Patent: Oct. 18, 2016

(54) DELAYING THE ONSET OF MUSCLE FATIGUE ASSOCIATED WITH FUNCTIONAL ELECTRICAL STIMULATION

(71) Applicants: Lee Fisher, Pittsburg, OH (US); Ronald Triolo, Cleveland Heights, OH (US); Dustin J. Tyler, Highland Heights, OH (US)

(72) Inventors: Lee Fisher, Pittsburg, OH (US); Ronald Triolo, Cleveland Heights, OH (US); Dustin J. Tyler, Highland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/101,465

(22) Filed: Dec. 10, 2013

(65) Prior Publication Data
US 2014/0094872 A1 Apr. 3, 2014

Related U.S. Application Data

(63) Continuation-in-part of application No. 13/918,440, filed on Jun. 14, 2013.

(60) Provisional application No. 61/659,508, filed on Jun. 14, 2012.

(51) Int. Cl.
*A61N 1/372* (2006.01)
*A61N 1/36* (2006.01)
*A61N 1/05* (2006.01)

(52) U.S. Cl.
CPC ....... *A61N 1/37252* (2013.01); *A61N 1/36003* (2013.01); *A61N 1/36146* (2013.01); *A61N 1/0556* (2013.01)

(58) Field of Classification Search
CPC ............... A61N 1/36146; A61N 1/36003; A61N 1/37252; A61N 1/0556
USPC ........... 600/595; 607/118, 48, 49, 50, 51, 52
See application file for complete search history.

(56) References Cited

U.S. PATENT DOCUMENTS

| | | | |
|---|---|---|---|
| 5,507,788 A * | 4/1996 | Lieber | A61N 1/36003 607/48 |
| 2010/0145221 A1* | 6/2010 | Brunnett | A61B 5/0488 600/554 |

* cited by examiner

*Primary Examiner* — Alyssa M Alter
(74) *Attorney, Agent, or Firm* — Tarolli, Sundheim, Covell & Tummino LLP

(57) ABSTRACT

The present invention relates a system that can configure a stimulus for functional electrical stimulation ("FES") to maintain a constant muscle force while delaying the onset of muscle fatigue and a related method of use. The stimulus can be delivered to a nerve via a set of multiple electrode contacts according to a stimulation parameter that maximizes a joint moment associated with the stimulus and minimizes the overlap between pairs of contacts. The joint moment can be related to the muscle force, and the overlap can be related to the onset of muscle fatigue.

20 Claims, 5 Drawing Sheets

DELAYING THE ONSET OF MUSCLE FATIGUE ASSOCIATED WITH FUNCTIONAL ELECTRICAL STIMULATION

RELATED APPLICATIONS

This application is a continuation-in-part of U.S. application Ser. No. 13/918,440, filed Jun. 14, 2013, and entitled SYSTEM AND METHOD FOR STIMULATING MOTOR UNITS, which claims the benefit of U.S. Provisional Application No. 61/659,508, filed Jun. 14, 2012. The entirety of the subject matter of these applications is hereby incorporated by reference for all purposes.

TECHNICAL FIELD

The present invention relates generally to functional electrical stimulation ("FES") and, more specifically, to a FES system that can maintain a constant muscle force while delaying the onset of muscle fatigue and related methods of use.

BACKGROUND

Functional electrical stimulation ("FES") is a technique that restores function to one or more paralyzed muscles, enabling patients suffering from paralysis due to spinal cord injury ("SCI"), head injury, stroke, or other neurological disorder to participate in activities that would not otherwise be possible. For example, a FES standing system stimulates motor units associated with standing to allow a SCI patient to stand for a period of time. For the patient's safety while standing, the FES standing system must ensure that the knees remain locked by delivering a maximal level of constant stimulation. However, the maximal level of stimulation can also cause muscle fatigue that can limit the standing time provided by the FES standing systems.

SUMMARY

In one aspect, the present invention includes a method for functional electrical stimulation ("FES") that can configure a stimulus to be provided to a nerve via a set of multiple electrode contacts. The acts of the method can be performed by a system comprising a processor (e.g., a FES system, a component of the FES system, etc). The stimulus can be configured according to a stimulation parameter that can be determined based on a first model of the joint moment that is based on a sum of moments generated from stimulus pulses from each contact and a second model of the overlap between pairs of electrode contacts.

In another aspect, the present invention includes a system that can configure a stimulus to be provided via a set of multiple electrode contacts to produce a constant muscle force while delaying the onset of muscle fatigue. The system includes a memory storing machine readable instructions and a processor, coupled to the memory, to facilitate execution of the machine readable instructions to at least: provide a first model of a joint moment based on a sum of moments generated from stimulus pulses applied to a nerve by each contact of a set of multiple electrode contacts; provide a second model of an overlap between pairs of contacts; and optimize a cost function based on the first model and the second model to provide a stimulation parameter that configures the stimulus.

In a further aspect, the present invention includes a non-transitory computer-readable device storing instructions executable by an associated processor to perform operations that configure a stimulus to be provided to a nerve via a set of multiple electrode contacts to produce a constant muscle force while delaying the onset of muscle fatigue. The operations include: determining a first model of a joint moment based on a sum of moments generated from stimulus pulses applied to the nerve by each contact; determining a second model of overlap between pairs of contacts; and determining a stimulation parameter that maximizes the joint moment and minimizes the overlap based on an optimization of a function of the first model and the second model.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
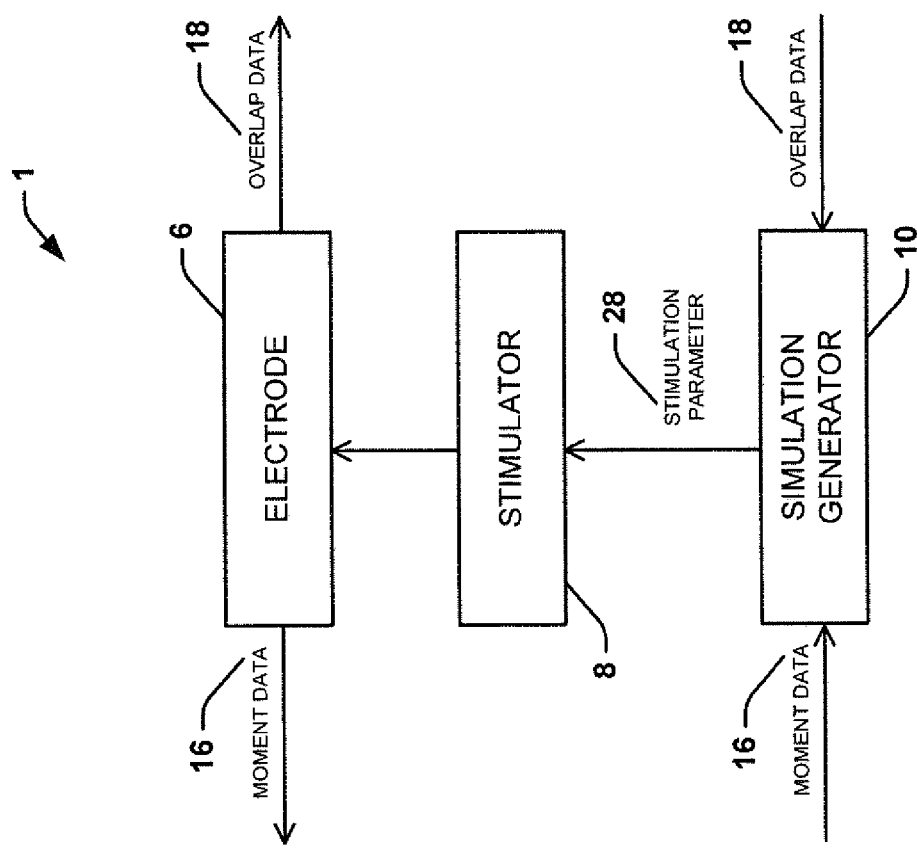
FIG. 1 is a schematic diagram of an example of a system that can configure a stimulus for functional electrical stimulation ("FES") in accordance with an aspect of the present invention.

The present invention generally relates to functional electrical stimulation ("FES"). The term "FES," as used herein, generally refers to a technique that can restore a motor function to a paralyzed patient. As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. More specifically, FES can restore the function to the paralyzed patient via an application of an electrical stimulus (e.g., one or more time-varying current waveforms) to multiple motor units that can coordinate a muscle contraction. The term "motor unit," as used herein, generally refers to a motor neuron and a skeletal muscle fiber innervated by the motor neuron, and a "muscle" generally includes a plurality of muscle fibers that are part of a corresponding plurality of motor units. As used herein, the term "joint moment" generally refers to a moment of force produced across a joint associated with the muscle based on a force associated with the muscle contraction. The joint moment is associated with the muscle contraction and associated muscle force.

Many FES systems apply a constant electrical stimulus (e.g., current stimulus) to motor units to ensure that a strong muscle contraction is maintained. However, the utility of these FES systems can be limited because the constant electrical stimulus can induce rapid muscle fatigue. By employing a time-varying electrical stimulus (with a plurality of corresponding stimulus waveforms) through an electrode that includes a set of multiple electrode contacts (e.g., provided by a multi-contact electrode and/or by a plurality of single contact electrodes) and producing a stimulation parameter of the electrical stimulus (e.g., a phase shift value, a pulse width value, a pulse amplitude value, a pulse frequency value, a total charge value, and/or a different adjustable parameter varying in a sinusoidal manner that facilitates selective stimulation of the nerve), the FES system of the present invention can stimulate a plurality of mutually agonist motor units to maintain a strong muscle contraction with constant muscle force (and corresponding constant joint moment) while delaying the onset of the muscle fatigue (e.g., by reducing the duty cycle of stimulation and/or minimizing the overlap between individual electrode contacts).

The present invention includes reference to block diagrams and/or flowchart illustrations of methods, apparatus, systems and/or computer program products according to certain aspects of the present invention. It is understood that each block of the block diagrams and/or flowchart illustrations, and combinations of blocks in the block diagrams and/or flowchart illustrations, can represent aspects of the present invention that can be embodied in hardware and/or in software (including firmware, resident software, microcode, etc.). Software aspects of the present invention can be implemented by computer program instructions that can be stored in a non-transitory memory (e.g., any non-transitory medium that can contain or store the program instructions, including, but not limited to, a portable computer diskette; a random access memory; a read-only memory; an erasable programmable read-only memory (or Flash memory); and a portable compact disc read-only memory) and may executed by a processor of a general purpose computer, special purpose computer, and/or other programmable data processing apparatus. Upon execution, the functions/acts specified in the block diagrams and/or flowchart block or blocks can be implemented.

In the context of the present invention, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof. As used herein, the term "and/or" can include any and all combinations of one or more of the associated listed items. Additionally, it will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or acts/steps) is not limited to the order presented in the claims or figures unless specifically indicated otherwise.

In accordance with the present invention, FIG. 1 depicts an example of a FES system 1 that can configure an electrical stimulus of a nerve such that one or more components of the nerve can signal corresponding muscle fibers to provide a constant muscle force while delaying the onset of muscle fatigue. Examples of suitable applications of the FES system 1 include, but are not limited to, motor neural prostheses for: standing, walking, hand grasp, upper extremity function, and/or bowl, bladder, and erection control. The FES system 1 can include an electrode 6, a stimulator 8, and a stimulation generator 10. The electrode 6, the stimulator 8, and/or the stimulation generator 10 can be configured to communicate via one or more wired and/or wireless connections and can be configured to be implantable within the patient and/or external to the patient.

The electrode 6 can be configured to form an electrical interface with a component of the peripheral nervous system (the "component") to deliver an electrical stimulus to a plurality of independent, mutually agonist motor units associated with a muscle (or "plurality of motor units") to control the muscle and/or a function of the muscle associated with an application of the FES system 1. Examples of the component include, but are not limited to: a peripheral nerve, a fascicle, a synapse, a motor unit, etc. Although an electrode that is configured to be internal to the patient's body (e.g., an electrode that is in contact with a nerve and/or a muscle) is described herein, it will be understood that the electrode 6 can be located external to the patient's body (e.g., an electrode that contacts the skin).

The electrode 6 can be configured to deliver an electrical stimulus to the component via a set of multiple electrode contacts (also referred to as the "set of contacts"). The set of contacts can include N electrode contacts, where N is a positive integer greater than or equal to two. In an embodiment, N can be a positive integer greater than or equal to three. Each contact can be configured to provide the electrical stimulus (or a portion of the electrical stimulus) to the component to activate a corresponding portion of the plurality of motor units. It will be understood that due to the placement and/or shape of electrode 6 and/or the anatomical shape of the component, one or more of the individual electrode contacts may not be associated with any portion of the plurality of motor units.

The set of contacts can be provided by a multi-contact electrode and/or by a plurality of single contact electrodes. Accordingly, the set of contacts can include, but is not limited to, a multi-contact nerve cuff electrode (examples schematically illustrated in FIGS. 2 and 3), one or more epimysial electrodes, one or more intramuscular electrodes, one or more electrode arrays, and/or one or more intrafasicular electrodes. However, any type of electrode that can achieve a stable, selective, chronic interface with the associated component of the peripheral nervous system to enable control of a muscle and/or a functionality of the muscle is within the scope of the present invention.

Figure 2:
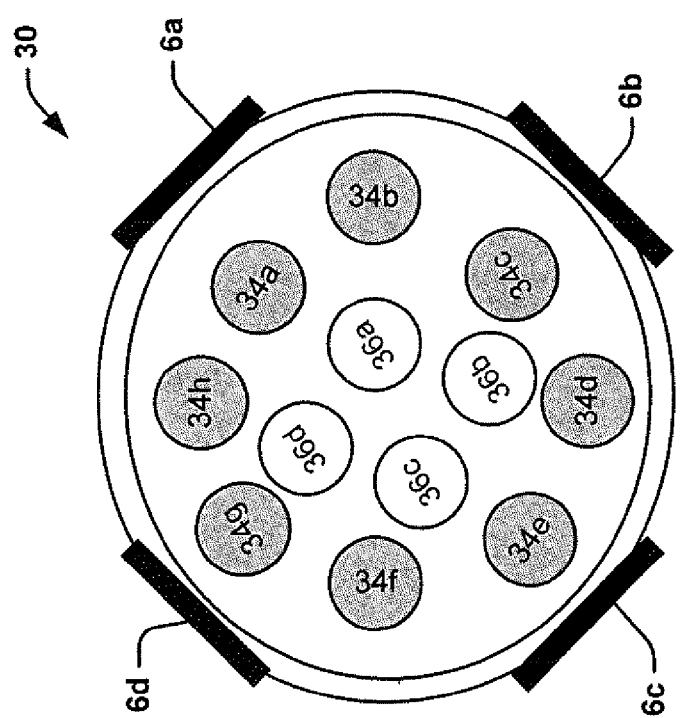

One example type of nerve cuff electrode, as illustrated in FIG. 2, is a self-sizing spiral nerve cuff electrode 30 (the "cuff electrode") that is configured to wrap around a portion a nerve, as shown in FIG. 2. The cuff electrode 30 has a circular cross-section and four electrode contacts 6a-6d that are spaced equally around the circumference of the nerve. Because the cuff electrode 30 is circular, it is well suited for interfacing with small circular nerves. However, the cuff electrode 30 may not be as appropriate for larger and/or non-circular (e.g., flatter) nerves at least because the electrode contacts 6a-6d preferentially stimulate a portion of the fascicles 34a-g within the nerve, but can leave other fascicles 36a-d (within the center of the cross section) unstimulated and/or stimulated to a lesser extent.

Figure 3:
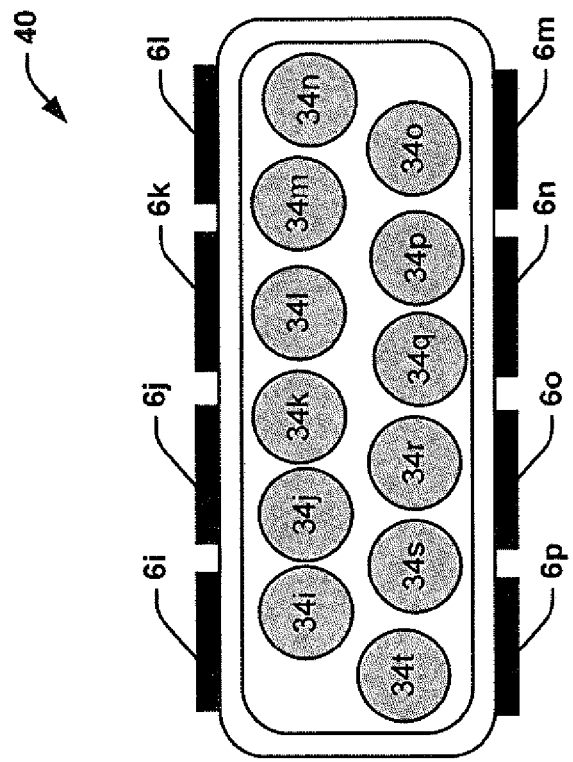
FIGS. 2 and 3 are schematic diagrams depicting examples of electrodes that each include a set of multiple electrode contacts in accordance with an aspect of the present invention.

Another example type of nerve cuff electrode, as illustrated in FIG. 3, is a flat interface nerve electrode (the "FINE") 40. In the example depicted in FIG. 3, the FINE 40 has a rectangular cross-section, which aligns the fascicles 42a-42i so that they are close enough to the eight stimulating contacts 42*a*-42*h* so that all of the fascicles can be stimulated. Accordingly, the FINE 30 may be better suited for larger and flatter nerves than the cuff electrode 30.

Referring again to FIG. 1, the stimulator 8 can be configured to configure the electrical stimulus according to a stimulation parameter 28 and to provide the configured electrical stimulus to the electrode 6 (e.g., via a stimulator assembly) for stimulation of the plurality of motor units. The stimulation generator 10 can be configured to adjust the stimulation parameter 28 to vary the number of motor units recruited at a time according to the electrical stimulus by each contact. The stimulation generator 10 can be located within the stimulator 8 and/or can be located independent from the stimulator 8. The stimulator 8 and/or the stimulation generator 19 can be configured to provide a control system and/or a power system for FES system 1. Although the stimulator 8 and the stimulation generator 10 are described as external to the patient's body herein, it will be understood that one or both of the stimulator 8 and/or the stimulation generator 10 can be implantable within the patient's body.

The electrical stimulus can include one or more time-varying current waveforms that can stimulate the plurality of motor units to induce one or more time-varying joint moments that can result in a constant joint moment that can correspond to a constant muscle force. In an embodiment, the electrical stimulus can include a plurality of time-varying current waveforms (the "plurality of waveforms"). As used for exemplary purposes herein, the plurality of waveforms can include sinusoidal waveforms. However, it will be understood that the plurality of waveforms are not limited to sinusoidal waveforms and can include other types of time varying current waveforms associated with one or more parameters that can be adjusted to produce a constant muscle force while delaying the onset of muscle fatigue (e.g., carousel waveforms, interleaved waveforms, etc.).

The stimulation parameter 28 can be associated with the one or more parameters related to the plurality of waveforms that can be delivered by the contacts to achieve selective stimulation of the plurality of motor units. In an example where the waveforms are sinusoidal waveforms, the stimulation parameter 28 can include, but is not limited to: a phase shift value, a pulse width value, a pulse amplitude value, a pulse frequency value, a total charge value, etc.

One example of an electrical stimulation that can be generated and configured by the stimulator 8 according to the stimulation parameter 28 is a sum of phase shifted sinusoids (the "SOPS") electrical stimulation. The stimulation parameter 28 of the SOPS electrical stimulation waveforms can be a pulse width parameter. The waveforms with different pulse widths can cause the joint moments generated by multiple independent motor unit populations to oscillate with equal amplitude and frequency, but offset phases, so that their combined output is a constant value equal to the sum of their average joint moments. For electrodes that can stimulate two or more independent populations of motor units, the total joint moment produced with the SOPS electrical stimulation will, by definition, be greater than the contribution of any single independent population of motor units. This allows a reduction in duty cycle as compared to constant stimulation and a corresponding reduction in fatigue, while still providing a high total joint moment. The SOPS electrical stimulation exhibits an improved circulation and oxygenation of the muscle tissue, a reduction of acidosis, a delay in depletion of glycogen and ATP stores within the muscle, and subsequent delay in the onset of muscle fatigue.

Figure 4:
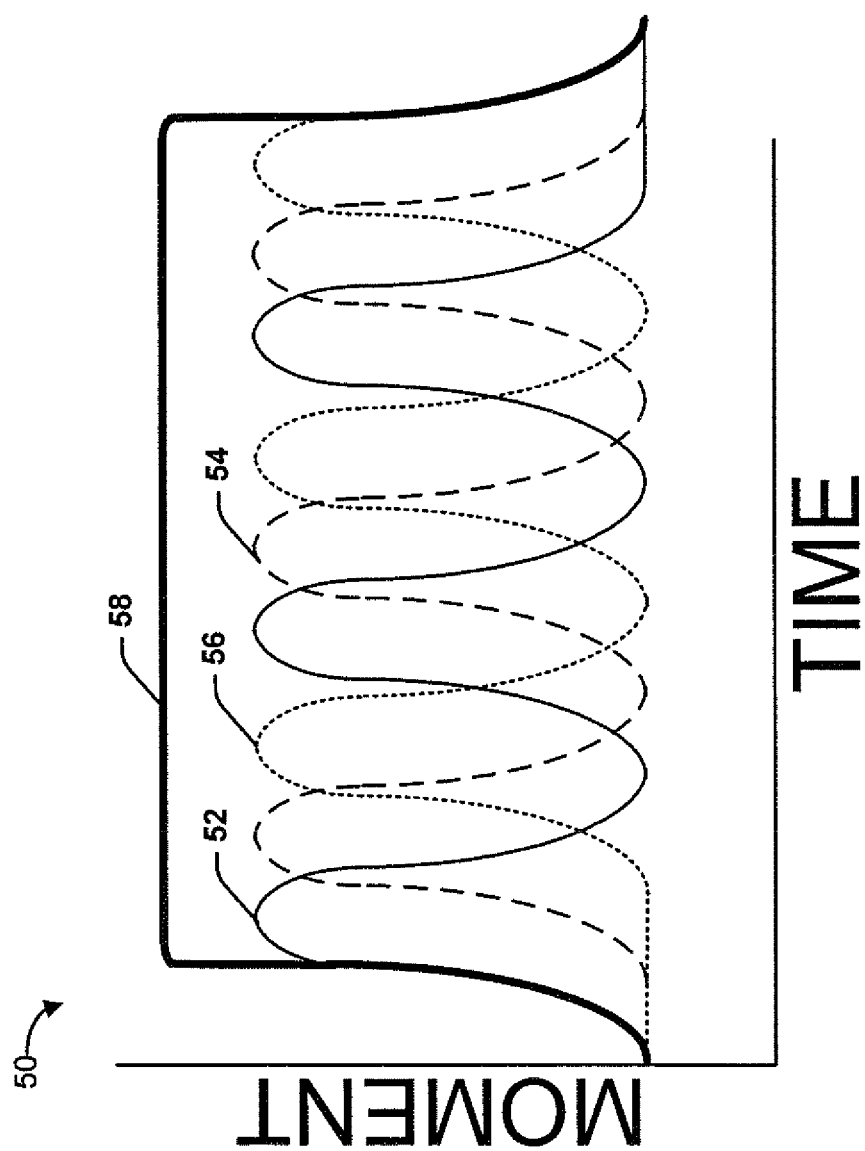
FIG. 4 is a schematic graph depiction of the time-varying joint moments associated with an example stimulation paradigm in accordance with an aspect of the present invention.

The SOPS electrical stimulation employs the mathematical identity that the sum of multiple sinusoids with equal amplitude and frequency with phase shift values evenly spread between 0° and 360° (0 and 2pi radians) will be constant and cancel the oscillations (or "ripple") in the resultant joint moment. As shown in FIG. 4, the moments generated by stimulating each of the three independent populations of motor units (e.g., 52, 54 and 56) oscillate between on and off and, because of their evenly distributed phase shifts values, the oscillations cancel out, resulting in a ripple-free constant joint moment 58 equal to the sum of the offsets of the oscillations.

Below is the mathematical derivation of an example of this relationship for three independent motor units or populations of motor units, but a similar approach could be taken for any number of independent populations of motor units greater than or equal to two.

Three isometric joint moments ($M_A$, $M_B$ and $M_C$) with oscillating magnitude, constant moment arm, and equally distributed phase are defined as:

$$M_A = r_A(\alpha_A \sin(\pi t) + \alpha_A); \quad \text{(Eq. 1)}$$

$$M_B = r_B(\alpha_B \sin(\pi t + 2/3\pi) + \alpha_B); \quad \text{(Eq. 2)}$$

$$M_C = r_C(\alpha_C \sin(\pi t + 4/3\pi) + \alpha_C); \quad \text{(Eq. 3)}$$

where $M_n$ is the joint moment produced by contact n, $r_n$ is the moment arm for motor units activated by contact n, $\alpha_n$ is the amplitude of the peak force generated by contact n, and $\alpha_n$ is the offset of the oscillations of contact n.

If all moments are agonists, and all moment arms are equal:

$$M_{total} = M_A + M_B + M_C \quad \text{(Eq. 4)}$$
$$= r \begin{pmatrix} a_A \sin(\pi t) + \alpha_A + a_B \sin(\pi t + 2/3\pi) + \\ \alpha_B + a_C \sin(\pi t + 4/3\pi) + \alpha_C \end{pmatrix}.$$

Using the trigonometric identity:

$$\sin(m + n) = \sin(m)\cos(n) + \cos(m)\sin(n), \quad \text{(Eq. 5)}$$

$$M_{total} = \quad \text{(Eq. 6)}$$
$$r(a_A \sin(\pi t) + \alpha_A + a_B(\sin(\pi t)\cos(2/3\pi) + \cos(\pi t)\sin(2/3\pi)) +$$
$$\alpha_B + a_C(\sin(\pi t)\cos(4/3\pi) + \cos(\pi t)\sin(4/3\pi)) + \alpha_C),$$

which can be simplified to:

$$M_{total} = \quad \text{(Eq. 7)}$$
$$r\left(a_A \sin(\pi t) + \alpha_a + a_B\left(-1/2\sin(\pi t) + \sqrt{3}/2\cos(\pi t)\right) + \alpha_B - \right.$$
$$\left. a_C\left(1/2\sin(\pi t) + \sqrt{3}/2\cos(\pi t)\right) + \alpha_C\right).$$

If $\alpha_A = \alpha_B = \alpha_C$, then the $\sin(\pi t)$ terms and the $\cos(\pi t)$ terms cancel out, leaving:

$$M_{total} = r(\alpha_A + \alpha_B + \alpha_C) \quad \text{(Eq. 8)}$$

In an implementation of the SOPS electrical stimulation with three independently stimulated motor units, each of the first, second, and third sinusoidally-varying moments can have a same amplitude, such that a sum of the moments provided across all of the plurality of motor units is substantially constant and non-zero. In accordance with an aspect of the invention, appropriate first, second, and third stimulation currents can be determined according to a model representing recruitment and overlap characteristics of first, second, and third motor units and their associated electrodes.

In order to achieve sinusoidal oscillations in joint moment, for each contact a pulse-width modulated isometric tetanic recruitment curve can be used as a transfer function between the desired joint moment and an estimate of the stimulation pattern required to generate it. For example, the recruitment curve can be created by applying three second trains of stimulus pulses through each contact with varied pulse widths (e.g., ranging from 1 to 255 µs) while the joint is held at a constant flexion and the joint moment is measured with respect to each stimulus pulse. The SOPS electrical stimulation can achieve ripple-free joint moment if the maximum joint moments generated by stimulating through all contacts are equal.

For example, if there are three independent agonist populations of motor units corresponding to three electrode contacts, and the joint moment produced by stimulating each population is made to oscillate at 0.2 Hz between 0 and 5 Nm, as long as the three sinusoids have phase shifts of 0°, 120° or 240°, the summed output will be ripple-free, with only the sum of their offsets remaining. This example would produce a constant 7.5 nm of knee extension moment, since the offset for each of the three sinusoids is 2.5 Nm.

Figure 5:
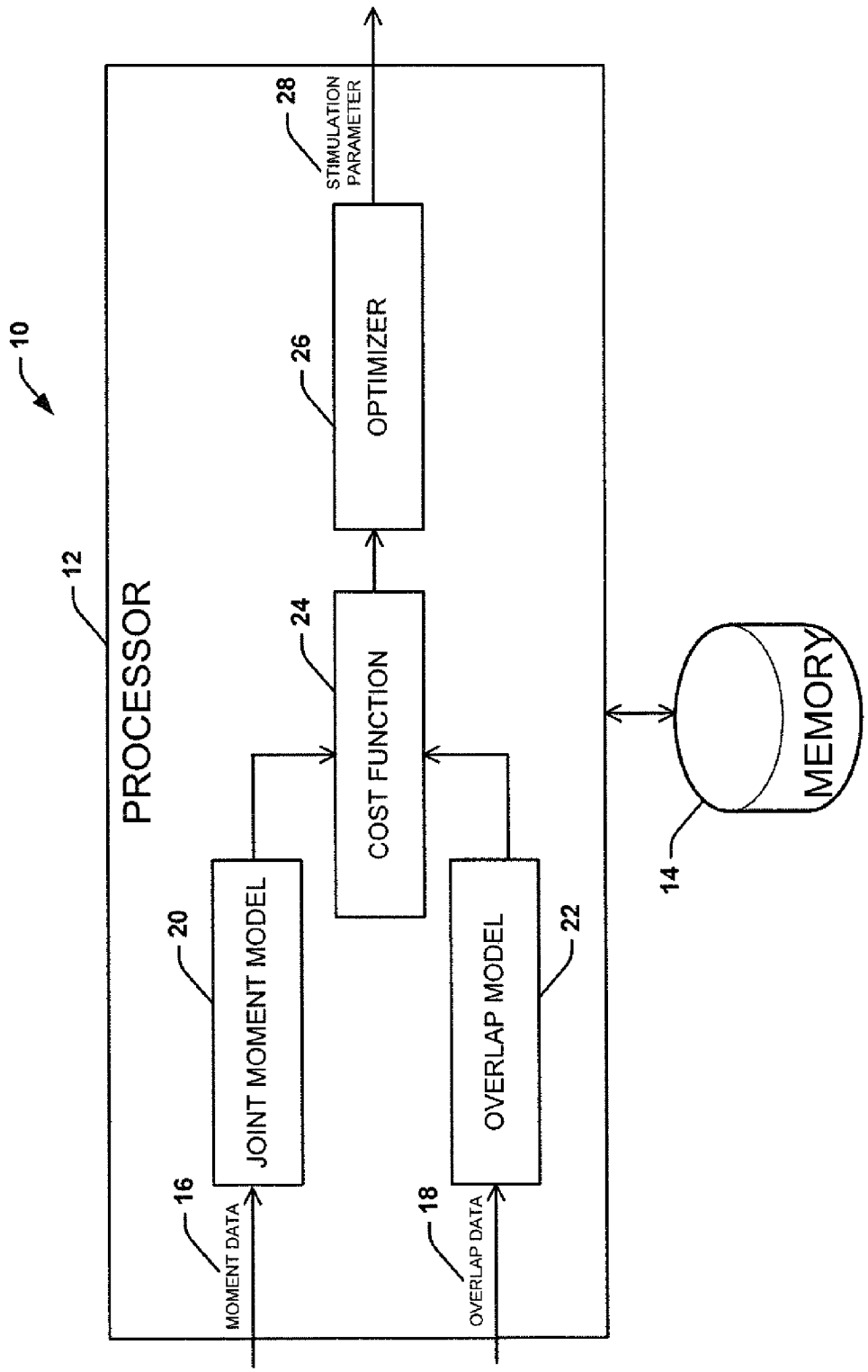
FIG. 5 is a schematic diagram of an example stimulation generator that can configure an electrical stimulus to maintain a constant muscle force while delaying the onset of muscle fatigue in accordance with an aspect of the present invention.

Referring again to FIG. 1, the stimulation generator 10 can receive moment data 16 corresponding to the joint moment associated with the electrical stimulation and overlap data 18 associated with the electrical stimulation, and can adjust the stimulation parameter 28 based on the moment data 16 and the overlap data 18. An example configuration of the stimulation generator 10 is illustrated in FIG. 5. The stimulation generator 10 can include a memory 14 (e.g., a non-transitory computer readable medium) to store computer program instructions that correspond to the adjustment of the stimulation parameter 28 and a processor 16 to execute the computer program instructions to adjust the stimulation parameter 28.

To achieve an electrical stimulation that can provide a constant muscle force (corresponding to a constant joint moment—by minimizing a ripple associated with a sinusoidal stimulation waveform) while delaying the onset of muscle fatigue (e.g., by reducing the duty cycle of stimulation and/or reducing the overlap between electrode contacts), the stimulation generator 10 can adjust the stimulation parameter 28 to maximize the joint moment and minimize the overlap. Accordingly, the stimulation generator 10 can determine a first model of the joint moment ("joint moment model" 20) based on the moment data 16 and a second model of the overlap ("overlap model" 22) based on the overlap data 18.

The moment data 16 can include data related to moments generated from individual contacts of the set of contacts. For example, the individual contacts of the set of contacts can receive a stimulus pulse and corresponding resultant joint moment can be recorded. The moment data 16 can also include a sum of the individual moments generated based on the stimulus pulses applied to each of the contacts individually. The overlap can correspond to pairs of contacts recruiting the same motor units, thereby increasing the likelihood of fatigue in the motor units that are jointly recruited.

The overlap data 18 can include data corresponding to an overlap between pairs of contacts from the set of contacts (e.g., shown between stimulations of the individual contacts delayed by a short time interval). The overlap data 18 can exclude data related to adjacent contacts from the set of contacts. For example, pairs of contacts of the set of contacts that are not adjacent to each other can be determined from the overlap model 22.

The stimulation generator 10 can employ a cost function 24 based on the joint moment model 20 and the overlap model 22 to adjust the stimulation parameter 28 to a value that creates the electrical stimulus that can produce a maximal joint moment and a minimal overlap. In an example, the cost function 24 can be a function of the stimulation parameter 28. The cost function can also be a function of the joint moment model 20 and the overlap model 22 (which can be scaled by weighting factors). The cost function can be, but is not limited to, a polynomial function, a sigmoid function, a Gaussian function, a Gompertz function, and/or a multi-dimensional polynomial function An example derivation of a cost function by the stimulation generator 10 based on the joint moment model 20 and the overlap model 22 is described below. In this example, the stimulation parameter 28 can be the pulse width of the sinusoidal stimulation waveforms (however, other stimulation parameters can form cost functions in a similar manner).

The cost function 24 can be of the form:

$$C(\overline{PW}) = -\omega_0 M_T(\overline{PW}) + \omega_1 O_T(\overline{PW}), \quad \text{(Eq. 9)}$$

where PW is an N-dimensional vector of pulse widths of stimulus pulses for an N-contact electrode, $O_T$ quantifies the overlap of all contacts within the electrode, $M_T$ quantifies the joint moment generated by all contacts within the electrode, and $\omega_o$ and $\omega_1$ are weighting factors that can be chosen to emphasize larger joint moments or smaller overlap. A penalty term can be added to the cost function in cases where the joint moment is less than a first threshold value (e.g., 5 Nm) and/or the overlap is greater than a second threshold value (e.g., 10%).

The joint moment term (or joint moment model 20), $M_T$, can be defined in this example as:

$$M_T(\overline{PW}) = \frac{\sum_{i=1:N} M_i(PW_i)}{\sum_{i=1:N} \max(M_i)}, \quad \text{(Eq. 10)}$$

where $M_i$ is the moment generated when stimulating through contact i. As an example, $M_i$ can be based on data related to recruitment of motor units by the corresponding stimulus. The data related to the recruitment can be based on twitch responses of the muscle associated with the joint moment associated. The twitch response can be linearly related to a tetanic response (corresponding to the constant muscle force and constant joint moment); for example, the twitch response and the tetanic response can be related according to a linear scaling factor that can be determined based on a ratio of a maxima of a twitch response curve to a maxima of a tetanic response curve. The data related to the recruitment can, additionally or alternatively, be defined by a user.

In the $M_T$ function, the sum of the moment functions from stimulating through each contact is divided by the sum of the maxima of the moment functions to normalize the joint moment term. In this way, the overall joint moment is normalized with respect to the overlap term, but joint moments from each of the contacts are treated equally with respect to each other.

The overlap term (or overlap model 22) can be defined in this example as follows. Overlap for a pair of contacts is quantified by the deviation from linear addition when stimulation is applied through one contact shortly after stimulation through another contact. This can be expressed as:

$$M_{i \cap j}(PW_i, PW_j) = M_i(PW_i) + M_j(PW_j) - M_{i \cup j}(PW_i, PW_j) \quad \text{(Eq. 11)}$$

where $M_{i \cap j}$ is the overlap between contacts i and j, $M_i$ and $M_j$ are the moments generated when stimulating through contacts i and j, respectively, and $M_{i \cup j}$ is a mathematical function fit to the moment generated when stimulating through two contacts with a short time delay. To take all of these pairwise overlaps into account, while normalizing the overlap so that its weighting is controlled relative to $M_T$, $O_T$ is defined as:

$$O_T(\overline{PW}) = \frac{2}{N^2 - N} \sum_{i=1:N-1} \sum_{J=2:N} \frac{M_{i \cap j}(PW_i, PW_j)}{M_{i \cup j}(PW_i, PW_j)} \quad \text{(Eq. 12)}$$

which ranges between 0 and 1. The overlap between pairs of contacts can vary over time (e.g., as a result of changes in the electrode-nerve interface, because the relative strength of the response through individual contacts is used in the calculation of the overlap, etc.), so the overlap model may be recalculated periodically or at any time deemed necessary over an extended period of time.

The stimulation generator 10 can also include an optimizer 26 that can adjust the stimulation parameter 28 in view of an optimization of the cost function 24. For example, the optimizer 26 can minimize the cost function 24 to determine the stimulation parameter 28 that can configured the electrical stimulus to produce a constant contraction (or constant joint moment) with a delayed onset of fatigue. In the case where the stimulation waveforms are sinusoidal, the stimulation parameter can be chosen such that the constant contraction can be a contraction that is virtually free from ripple.

The optimizer 26 can employ an optimization algorithm to optimize the cost function 24 so that the stimulation parameter 28 can be determined. The optimization algorithm can minimize the cost function 24 to determine an optimal stimulation parameter 28 that can maximize the joint moment and minimize the overlap. As an example, the optimization algorithm can be a direct search optimization algorithm. It will be understood that other types of optimization algorithms can be used to adjust the stimulation parameter.

While aspects of the present invention have been particularly shown and described with reference to the embodiment of system 1, it will be understood by those of ordinary skill in the art that various additional embodiments may be contemplated without departing from the spirit and scope of the present invention. For example, the specific configuration and application of system 1 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials such as, but not limited to, stainless steel, titanium, platinum, Nitinol, epoxies, urethanes, metals, polymers, ceramics, and the like; however, the chosen material(s) should be biocompatible for many applications of the present invention. Nerves, muscles, fascicles, and/or any other stimulated structures of the living body are described herein without restriction as "motor units" and/or "nerves", due to the integrated and connected nature of all of these structures with respect to the described use environments. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Other electrode designs and stimulation paradigms could be provided, such as, but not limited to, field steering, bipolar or tripolar electrode configurations, and/or different geometries such as a flat cuff cross-section to further improve selectivity and performance.

Figure 6:
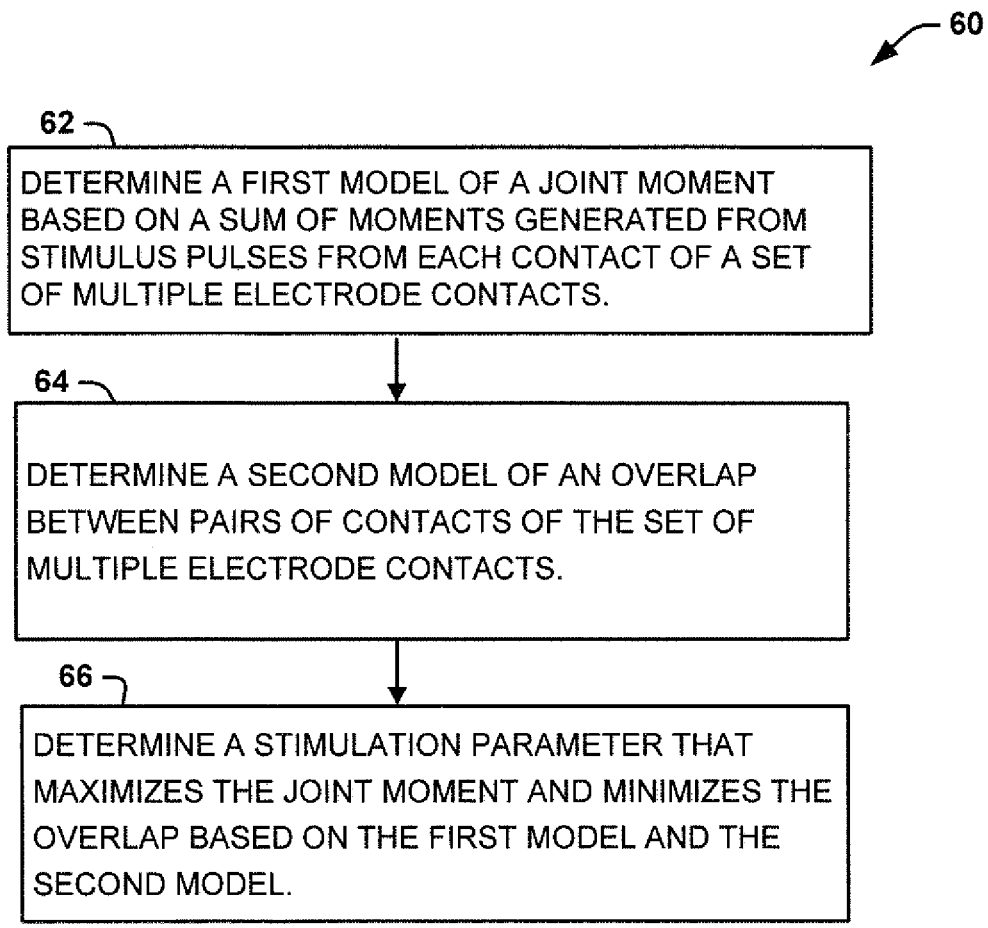
FIG. 6 is a schematic process flow diagram depicting an example of a method that can configure an electrical stimulus for FES in accordance with an aspect of the present invention.

In view of the foregoing structural and functional features described above, a method 60 in accordance with various aspects of the present invention will be better appreciated with reference to FIG. 6. While, for purposes of simplicity of explanation, the method 60 of FIG. 6 is shown and described as executing serially, it is to be understood and appreciated that the present invention is not limited by the illustrated order, as some aspects could occur in different orders and/or concurrently with other aspects shown and described herein. Moreover, not all illustrated aspects may be required to implement method 60. It will be appreciated that the illustrated aspects of method 60 can be implemented in whole or in part as machine-executable instructions stored on a non-transitory computer readable device (e.g., memory 14). The instructions can be executed by a processing device (e.g., processor 12) to facilitate the performance of the operations of the method 60.

FIG. 6 illustrates an example of a method 60 for configuring a stimulus to be provided to a nerve via a set of multiple electrode contacts (e.g., provided by electrode 6, which can be a multi-contact electrode with contacts 6a-h or 6i-p and/or a plurality of single-contact electrodes) for functional electrical stimulation (e.g., to produce a constant muscle force while delaying the onset of muscle fatigue). At 62, a first model of a joint moment (e.g., joint moment model 20) is determined (e.g., by stimulation generator 10) based on a sum of moments (e.g., moment data 16) generated from stimulus pulses applied to a nerve innervating a muscle by each contact (e.g., each contact receives the respective stimulus pulse in sequence) of a set of contacts. At 64, a second model of an overlap between pairs of contacts (e.g., adjacent pairs of contacts) of the set of contacts (e.g., overlap model 22) is determined (e.g., by stimulation generator 10) based on data representing the overlap (e.g., overlap data 18). At 66, based on the first model and the second model, a stimulation parameter (e.g., stimulation parameter 28) is determined (e.g., by optimizer 26 of stimulation generator 10) that maximizes the joint moment and minimizes the overlap.

From the above description, those skilled in the art will perceive improvements, changes and modifications. Such improvements, changes and modifications are within the skill of one in the art and are intended to be covered by the appended claims.

Having described the invention, we claim:

1. A method, comprising:
   determining, by a system comprising a processor, a stimulation parameter for a set of electrical stimulus waveforms to be applied to a nerve by a set of multiple electrode contacts, comprising:
      determining a first model of a joint moment based on a sum of moments generated from an electrical stimulus pulse from each contact of a set of multiple electrode contacts;
      determining a second model of an overlap between pairs of contacts of the set of multiple electrode contacts; and
      determining the stimulation parameter based on a function of the first model and the second model, wherein the stimulation parameter maximizes the joint moment and minimizes the overlap; and
   configuring, by the system, the set of electrical stimulus waveforms to be applied to the nerve by the set of multiple electrode contacts based on the stimulation parameter, wherein a stimulation of the nerve by the set of multiple electrode contacts applying the set of electrical stimulus waveforms results in a constant joint moment.

2. The method of claim 1, wherein the sum of moments corresponds to a sum of twitch responses of the muscle to the stimulus pulses from each contact of a set of multiple electrode contacts.

3. The method of claim 1, wherein the stimulation parameter comprises at least one of a phase shift value, a pulse width value, a pulse amplitude value, a pulse frequency value, a total charge value, or an adjustable parameter varying in a sinusoidal manner that facilitates selective stimulation of the nerve.

4. The method of claim 1, wherein the set of electrical stimulus waveforms comprises a plurality of sinusoidal waveforms each comprising a phase that is evenly spread between 0 degrees and 360 degrees.

5. The method of claim 1, wherein the stimulation parameter delays an onset of fatigue of a muscle associated with the joint.

6. The method of claim 1, wherein the function comprises a polynomial function, a sigmoid function, a Gaussian function, a gompertz function, a multi-dimensional polynomial function, or another appropriate mathematical representation.

7. The method of claim 1, wherein the stimulation parameter minimizes a ripple in the joint moment over time.

8. The method of claim 1, wherein the determining the second model further comprises eliminating non-adjacent pairs of contacts of the set of multiple electrode.

9. A system, comprising:
   a memory storing machine readable instructions; and
   a processor, coupled to the memory, to facilitate execution of the machine readable instructions to at least:
      provide a first model of a joint moment based on a sum of moments generated from stimulus pulses applied to a nerve innervating a muscle by each contact of a set of multiple electrode contacts;
      provide a second model of an overlap between pairs of contacts of the set of multiple electrode contacts;
      optimize a cost function based on the first model and the second model to provide a stimulation parameter that maximizes the joint moment and minimizes the overlap; and
      configure a set of electrical stimulus waveforms to be applied to a nerve by the set of multiple electrode contacts based on the stimulus parameter, wherein a stimulation of the nerve by the set of multiple electrode contacts applying the set of electrical stimulus waveforms results in a constant joint moment.

10. The system of claim 9, wherein the sum of moments corresponds to a sum of twitch responses of the muscle to the stimulus pulses.

11. The system of claim 9, wherein the overlap is identified for each pair when the corresponding pair of moments deviates from linear addition.

12. The system of claim 9, wherein the set of multiple electrode contacts comprises at least 2 electrode contacts.

13. The system of claim 9, wherein the stimulation parameter delays an onset of fatigue of a muscle associated with the joint by intermittently activating the at least two independent motor units.

14. The system of claim 9, wherein the model of joint moment or the model of overlap is user definable.

15. A non-transitory computer-readable device storing instructions executable by an associated processor to perform operations, comprising:
   determining a first model of a joint moment based on a sum of moments generated from stimulus pulses applied by each contact of a set of multiple electrode contacts;
   determining a second model of overlap between pairs of contacts of the set of multiple electrode contacts; and
   determining a stimulation parameter that maximizes the joint moment and minimizes the overlap based on an optimization of a function of the first model and the second model; and
   configuring a set of electrical stimulus waveforms to be applied to a nerve by the set of multiple electrode contacts based on the stimulation parameter to ensure a constant joint moment.

16. The non-transitory computer-readable device of claim 15, wherein the overlap is related to a fatigue of a muscle associated with the nerve.

17. The non-transitory computer-readable device of claim 16, wherein the overlap is related to the pairs of contacts recruiting the same motor unit.

18. The non-transitory computer-readable device of claim 15, wherein
   the function is a cost function of the first model and the second model, and
   the providing the stimulation parameter further comprises minimizing the cost function to provide the stimulation parameter.

19. The non-transitory computer-readable device of claim 16, wherein
   the stimulation parameter comprises an adjustable parameter of a plurality of sinusoidal stimulation waveforms in the sum of phase shifted sinusoids electrical stimulation.

20. The non-transitory computer-readable device of claim 19, wherein the common feature comprises a common amplitude or a common frequency.

* * * * *